(12) United States Patent
Nakamura

(10) Patent No.: US 10,139,370 B2
(45) Date of Patent: Nov. 27, 2018

(54) INSPECTION DEVICE AND METHOD FOR DISPOSING MAGNETO-OPTICAL CRYSTAL

(71) Applicant: HAMAMATSU PHOTONICS K.K., Hamamatsu-shi, Shizuoka (JP)

(72) Inventor: Tomonori Nakamura, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/314,657

(22) PCT Filed: Jun. 2, 2015

(86) PCT No.: PCT/JP2015/065932
§ 371 (c)(1),
(2) Date: Nov. 29, 2016

(87) PCT Pub. No.: WO2015/186711
PCT Pub. Date: Dec. 10, 2015

(65) Prior Publication Data
US 2017/0199154 A1 Jul. 13, 2017

(30) Foreign Application Priority Data
Jun. 4, 2014 (JP) .................... 2014-115568

(51) Int. Cl.
*H01F 1/00* (2006.01)
*H04N 9/47* (2006.01)
(Continued)

(52) U.S. Cl.
CPC .............. *G01N 27/72* (2013.01); *G01R 31/26* (2013.01); *G01R 31/2601* (2013.01);
(Continued)

(58) Field of Classification Search
CPC .... G01N 27/72; G01R 31/308; G01R 33/032; G01R 31/2601
(Continued)

(56) References Cited

U.S. PATENT DOCUMENTS 5,149,962 A 9/1992 Maurice
2010/0006771 A1 1/2010 Miyazaki
(Continued)

FOREIGN PATENT DOCUMENTS

CN 101675344 A 3/2010
CN 103635818 A 3/2014
(Continued)

OTHER PUBLICATIONS

WO2014/050907; Otani et al., Steel Sheet Inspection Apparatus 2014.*
(Continued)

*Primary Examiner* — Farhana Hoque
(74) *Attorney, Agent, or Firm* — Drinker Biddle & Reath LLP

(57) ABSTRACT

An inspection device includes a light source, an MO crystal disposed to face a semiconductor device (D), an object lens configured to concentrate the light output from the light source onto the MO crystal, a holder configured to hold the MO crystal, a flexible member interposed between the MO crystal and the holder, and an object lens drive unit configured to cause the MO crystal to contact the semiconductor device (D) by causing the holder to be moved in the optical axis direction of the object lens, wherein, when the MO crystal contacts the semiconductor device (D), the flexible member is bent, so that an incident plane is inclined in a range in which an inclination angle of the incident plane of the light in the MO crystal with respect to a plane orthogonal to the optical axis is less than or equal to an aperture angle.

13 Claims, 13 Drawing Sheets

(51) Int. Cl.
*G01N 27/72* (2006.01)
*G01R 33/032* (2006.01)
*G01R 31/26* (2014.01)
*G01R 31/28* (2006.01)
*G01R 31/308* (2006.01)

(52) U.S. Cl.
CPC ........... *G01R 31/28* (2013.01); *G01R 31/308* (2013.01); *G01R 33/032* (2013.01)

(58) Field of Classification Search
USPC .................. 324/750.23; 148/121; 348/92
See application file for complete search history.

(56) References Cited

U.S. PATENT DOCUMENTS

| | | | | |
|---|---|---|---|---|
| 2012/0274931 | A1* | 11/2012 | Otani | G01N 21/21 356/237.3 |
| 2014/0176698 | A1* | 6/2014 | Banerjee | G01N 21/21 348/92 |
| 2015/0253242 | A1* | 9/2015 | Ito | G01N 21/86 148/121 |

FOREIGN PATENT DOCUMENTS

| | | |
|---|---|---|
| JP | S63-131116 | 6/1988 |
| JP | H04-313057 A | 11/1992 |
| JP | H05-281313 A | 10/1993 |
| JP | H07-218425 A | 8/1995 |
| JP | 2004-087141 | 3/2004 |
| JP | 2005-241489 A | 9/2005 |
| JP | 2005-293865 | 10/2005 |
| JP | 2006-300879 A | 11/2006 |
| JP | 2013-544352 A | 12/2013 |
| WO | WO-2012/049538 A1 | 4/2012 |
| WO | WO-2014/050907 A1 | 4/2014 |

OTHER PUBLICATIONS

WO2012/049538; Banerjee et al., System and Methods for Imaging Characteristics of a sample and for identifying regions of damage in the sample 2014.*

H. Nasuno et al., "Magnetic Field Waveform Measurement Using Pulsed Laser," Journal of the Magnetics Society of Japan, 2011, pp. 273-276, vol. 35, No. 3 [including English translation].

International Preliminary Report on Patentability dated Dec. 15, 2016 for PCT/JP2015/065932.

* cited by examiner

INSPECTION DEVICE AND METHOD FOR DISPOSING MAGNETO-OPTICAL CRYSTAL

TECHNICAL FIELD

Aspects of the present invention relate to an inspection device and a method of disposing a magneto-optical crystal using optical probing technology.

BACKGROUND ART

As technology for inspecting a measurement object such as an integrated circuit, there is an optical probing technology for radiating light emitted from a light source to a measurement object and detecting measurement light (reflected light) from the measurement object by a light sensor to acquire a detection signal. In this optical probing technology, a method of disposing a magneto-optical (MO) crystal (e.g., see Patent Literature 1 and 2) facing an optical irradiation plane of a measurement object and acquiring a detection signal by detecting reflected light according to a magneto-optical effect of the MO crystal is known.

CITATION LIST

Patent Literature

[Patent Literature 1] Japanese Unexamined Patent Publication No. 2005-241489

Non-Patent Literature

[Non-Patent Literature 1] "Magnetic field waveform measurement using pulsed laser," J. Magn. SOC. Jpn., 35, 273-276 (2011)

SUMMARY OF INVENTION

Technical Problem

In the method using the above-described MO crystal, as illustrated in FIG. 13, the MO crystal is fixed to a lens plane of a lens used for light concentration (e.g., an object lens). The lens is close to an optical irradiation plane of the measurement object and a magnetic field generated in the measurement object is measured. However, if the measurement object is inclined, a distance between the measurement object and the MO crystal may not be sufficiently short. In this case, the detection accuracy of a detection signal may be degraded by the degradation of detection sensitivity or the like. Therefore, an objective of an aspect of the present invention is to provide an inspection device and a method of disposing a magneto-optical crystal for improving detection accuracy of a detection signal.

Solution to Problem

An inspection device according to an aspect of the present invention is an inspection device including: a light source configured to output light; a magneto-optical crystal disposed to face a measurement object; a lens unit configured to concentrate the light onto the magneto-optical crystal; a holder unit configured to hold the magneto-optical crystal; a flexible member interposed between the magneto-optical crystal and the holder unit; and a drive unit configured to cause the magneto-optical crystal to contact the measurement object by moving the holder unit in an optical axis direction of the lens unit, wherein, when the magneto-optical crystal contacts the measurement object, the flexible member is bent, so that an incident plane is able to be inclined in a range in which an inclination angle of the incident plane of the light in the magneto-optical crystal with respect to a plane orthogonal to the optical axis is less than or equal to an aperture angle of the lens unit.

A method of disposing a magneto-optical crystal according to an aspect of the present invention is a method of disposing a magneto-optical crystal facing a measurement object, wherein a holder holds the magneto-optical crystal via a flexible member, the method including: disposing the magneto-optical crystal on an optical axis of an object lens; causing the magneto-optical crystal to contact the measurement object by moving the holder in an optical axis direction of the lens unit; and inclining an incident plane in a range in which an inclination angle of the incident plane of the light in the magneto-optical crystal with respect to a plane orthogonal to the optical axis is less than or equal to an aperture angle of the lens unit by bending the flexible member when the magneto-optical crystal contacts the measurement object.

In the inspection device and the method of disposing the magneto-optical crystal, the flexible member is bent when the magneto-optical crystal contacts the measurement object, so that the incident plane of light of the magneto-optical crystal can be inclined with respect to the plane orthogonal to the optical axis. Here, if the measurement object is inclined with respect to the plane orthogonal to the optical axis, a part of the magneto-optical crystal to be moved by the drive unit which moves in the optical axis direction is pressed to the measurement object in advance of the other part. In this state, the drive unit moves further in the same direction, so that the flexible member is bent and the other part of the magneto-optical crystal is also pressed to the measurement object while being shaped to the inclined measurement object. That is, it is possible to set the incident plane of light of the magneto-optical crystal at an angle according to the inclination of the measurement object (along the inclination) using flexibility of the flexible member. Thereby, a state in which the measurement object and the magneto-optical crystal are in contact with each other (or a state in which they are in proximity to each other) is brought about and a magnetic field property occurring in the measurement object can be appropriately measured using the magneto-optical crystal. Also, because the inclination of the incident plane of the magneto-optical crystal is less than or equal to an aperture angle of the lens unit, it is possible to reliably detect reflected light by the magneto-optical crystal in the lens unit. From the above, the detection accuracy of the detection signal can be improved if the measurement object is inclined.

In the inspection device according to an aspect of the present invention, the flexible member may be interposed between the holder unit and the magneto-optical crystal in the optical axis direction. The flexible member is interposed between the holder unit and the magneto-optical crystal in the optical axis direction, i.e., a direction in which the holder unit (and the magneto-optical crystal held by the holder unit) moves, so that the flexible member can be appropriately bent according to a force generated by contacting when the magneto-optical crystal contacts the measurement object.

In the inspection device according to an aspect of the present invention, an opening through which light from the light source is transmitted may be formed in the holder unit and the magneto-optical crystal may be interposed within a region of the opening as viewed from the optical axis direction. Thereby, when the magneto-optical crystal which moves in the optical axis direction contacts the measurement object, the flexible member is bent, so that it is possible to move the magneto-optical crystal to the inside of the opening and more appropriately press the magneto-optical crystal to the measurement object.

In the inspection device according to an aspect of the present invention, an opening through which the light is transmitted between the opening and the magneto-optical crystal may be formed in the flexible member. The opening is formed, so that the flexible member is more easily bent. Also, because it is possible to view the magneto-optical crystal from the opening, it is possible to easily cause the magneto-optical crystal to contact the measurement object.

In the inspection device according to an aspect of the present invention, the holder unit may be attached to the lens unit and the drive unit may move the holder unit in the optical axis direction of the lens unit and cause the magneto-optical crystal to contact the measurement object by moving the lens unit in the optical axis direction. Thereby, the movement of the object lens and the movement of the holder unit may be simultaneously performed. Also, the holder unit may have a first holding unit which directly holds the magneto-optical crystal and a second holding unit which holds the first holding unit via the flexible member. The contacting of the magneto-optical crystal against the measurement object can be flexibly performed according to a shape of the measurement object or an inspection region by configuring the holder unit from two holding units of the first holding unit and the second holding unit. Also, it is possible to flexibly determine a position of the flexible member or the like. Further, because it is possible to make a configuration in which the flexible member and the magneto-optical crystal are not in direct contact with each other, it is possible to prevent the magneto-optical crystal from being invisible due to the flexible member.

In the inspection device according to an aspect of the present invention, the light output from the light source may be incoherent light. Thereby, it is possible to reduce noise due to interference of light within the magneto-optical crystal and between the magneto-optical crystal and the measurement object. Also, a wavelength of the light output from the light source may be 1064 nm or more. If the measurement object is a semiconductor device, the observation of the measurement object is possible.

In the inspection device according to an aspect of the present invention, the magneto-optical crystal may reflect a part of the light and transmit a part of the light. It is possible to cause the magneto-optical crystal to contact the measurement object while viewing a measurement position in the measurement object by imaging light transmitted through the magneto-optical crystal and reflected by the measurement object.

In the inspection device according to an aspect of the present invention, the flexible member may have elasticity. Thereby, it is possible to appropriately bend the flexible member and press the magneto-optical crystal to the measurement object.

In the inspection device according to an aspect of the present invention, the flexible member may be configured to include at least one of rubber, sponge, or an elastic membrane. Thereby, it is possible to appropriately bend the flexible member and set a state in which the measurement object and the magneto-optical crystal are in contact with each other (or a state in which they are in proximity to each other).

In the inspection device according to an aspect of the present invention, the flexible member may transmit light. Thereby, it is also possible to view the magneto-optical crystal via the flexible member and cause the magneto-optical crystal to contact the measurement object easily.

Advantageous Effects of Invention

According to an aspect of the present invention, it is possible to provide an inspection device in which the detection accuracy of a detection signal is improved.

DESCRIPTION OF EMBODIMENTS

Figure 1:
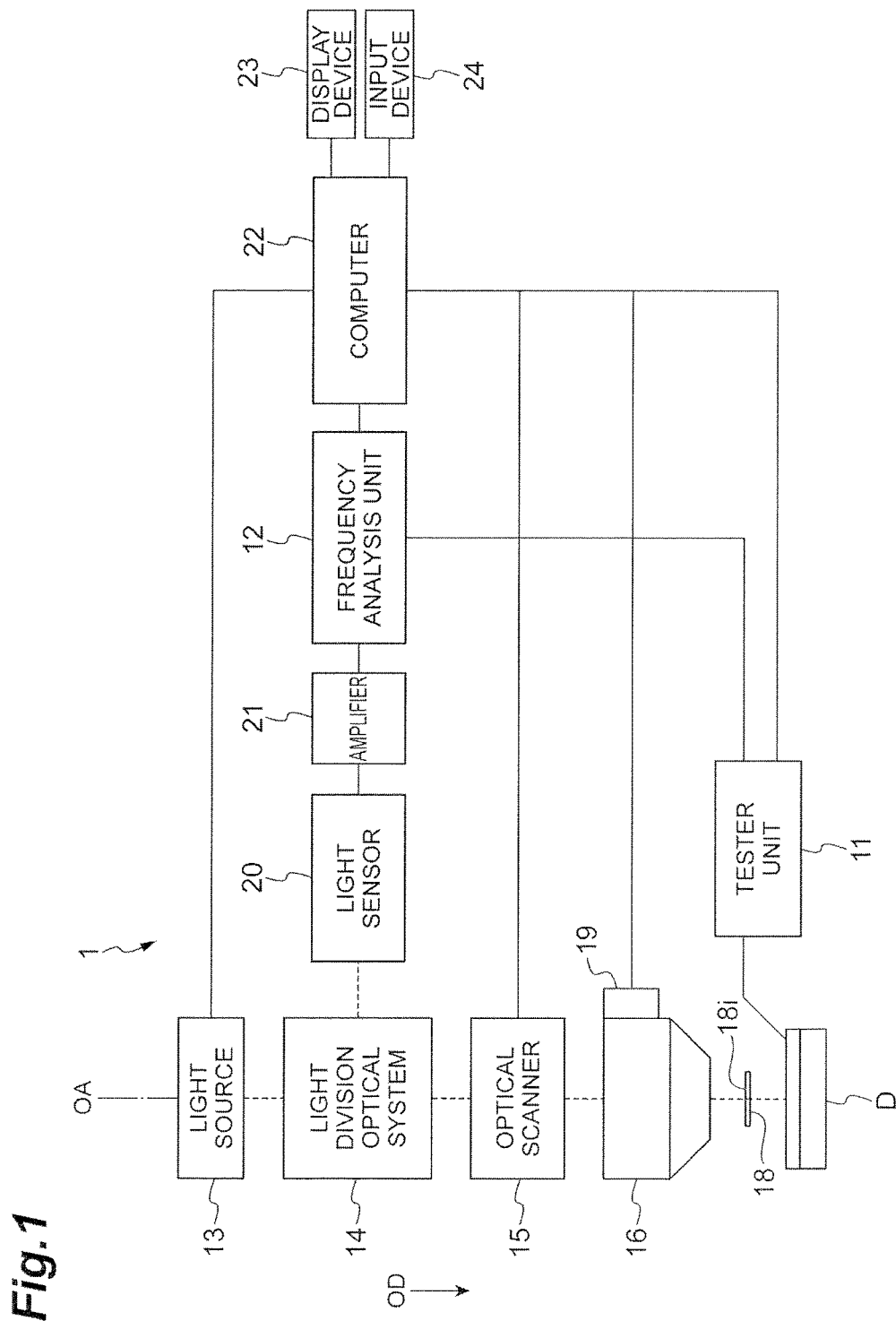
FIG. 1 is a configuration diagram of an inspection device of a first embodiment of the present invention.

Hereinafter, embodiments of the present invention will be described in detail with reference to the accompanying drawings. The same or corresponding parts are denoted by the same reference signs in the drawings and redundant description thereof will be omitted.

[First Embodiment]

As illustrated in FIG. 1, an inspection device 1 according to the first embodiment is a device for inspecting a semiconductor device D such as a device for specifying a position at which a malfunction has occurred in the semiconductor device D which is an inspected device (a device under test (DUT)) which is a measurement object. As the semiconductor device D, there are an integration circuit having a PN junction such as a transistor (e.g., small scale integration (SSI), medium scale integration (MSI), large scale integration (LSI), very large scale integration (VLSI), ultra large scale integration (VLSI), or giga scale integration (GSI)), a large current/high voltage MOS transistor, a bipolar transistor, and the like. Also, the measurement object may be, for example, a thin film transistor (TFT) such as an amorphous transistor, a polysilicon transistor, or an organic transistor formed on a glass plane or a package including a semiconductor device as well as the semiconductor device D and furthermore may be a composite substrate.

A tester unit 11 is electrically connected to the semiconductor device D via a device control cable. The tester unit 11 is operated by a power supply (not illustrated) and iteratively applies a predetermined modulated current signal (a test signal) to the semiconductor device D. In the semiconductor device D, a modulated magnetic field is generated according to the modulated current signal. A light sensor 20 to be described below detects an optical signal according to the modulated magnetic field, so that lock-in detection for detecting measured light at a specific frequency is enabled. Also, the tester unit 11 may not necessarily apply the modulated current signal and may apply a continuous wave (CW) current signal for generating pulse light according to a detected frequency. It is possible to improve S/N by performing the lock-in detection. The tester unit 11 is electrically connected to a frequency analysis unit 12 by a timing signal cable.

The inspection device 1 includes a light source 13. The light source 13 is operated by a power supply (not illustrated) and generates and outputs continuous wave (CW) light or pulse light to be radiated to an MO crystal 18 (a magneto-optical crystal) to be described below and the semiconductor device D. The light output from the light source 13 may be incoherent light or may be coherent light such as laser light. As the light source 13 which outputs incoherent light, a super luminescent diode (SLD), an amplified spontaneous emission (ASE) light source, a light emitting diode (LED), and the like can be used. As the light source 13 which outputs coherent light, a solid-state laser light source, a semiconductor laser light source, and the like can be used. Also, a wavelength of light to be output from the light source 13 may be 530 nm or more or 1064 nm or more. Light output from the light source 13 is guided to a light division optical system 14 via a polarization preserving single-mode optical coupler (not illustrated) and a polarization preserving single-mode optical fiber for probe light. The light guided from the light source 13 to the light division optical system 14 is further guided to an optical scanner 15. The light source 13, the light division optical system 14, and the optical scanner 15 are optically coupled. Details of the light division optical system 14 will be described below.

The optical scanner 15 is constituted of, for example, a light scanning element such as a galvano-mirror or a micro electro mechanical system (MEMS) mirror, and radiates (scans) light to a selected region (a spot or an area selected by a user) on an incident plane 18i of the MO crystal 18 to be described below. The selected region in the MO crystal 18 is a selected area or a selected spot to be two-dimensionally scanned by the optical scanner 15 controlled by a computer 22.

An object lens 16 (a lens unit) concentrates the light guided by the light division optical system 14 and the optical scanner 15 onto the MO crystal 18. The light division optical system 14, the optical scanner 15, the object lens 16, and the MO crystal 18 are optically coupled to one another. The object lens 16 is configured so that switching between a low-magnification object lens (e.g., 5×) and a high-magnification object lens (e.g., 50×) can be performed by a turret (not illustrated). A holder 17 (a holder unit) is connected to an adaptor 25 (see FIG. 2) capable of being attached to the object lens 16 and the holder 17 holds the MO crystal 18. Details of members related to the holder 17 will also be described with reference to FIG. 2. In FIG. 1, a configuration and a connection state between components illustrated in FIG. 2 are partially omitted.

Figure 2:
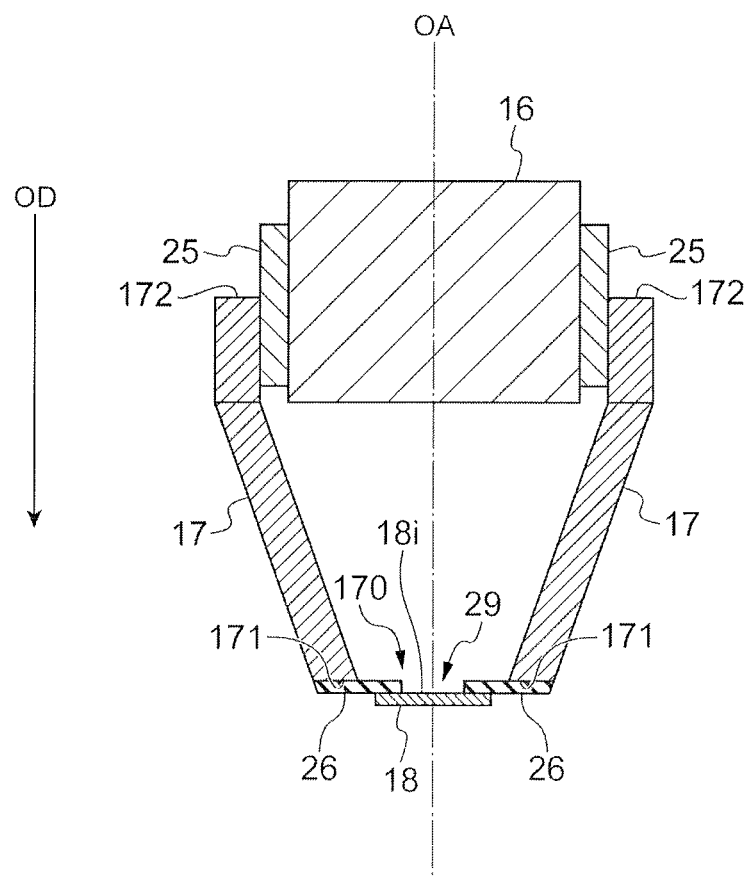
FIG. 2 is a cross-sectional view of a holder unit in the inspection device of FIG. 1.

As illustrated in FIG. 2, a hollow cylindrical adaptor 25 having an optical axis OA as the center of a diameter thereof is provided to cover the outer periphery of the object lens 16. Further, the holder 17 is provided to cover the outer periphery of the adaptor 25. The holder 17 is fixed to the adaptor 25 in a state in which an internal surface of one end 172 in an optical axis direction OD is in contact with an external surface of the adaptor 25. The holder 17 has approximately a truncated cone shape having an optical axis OA as the center of the diameter thereof and the diameter reduces from the one end 172 to the other end 171 in the optical axis direction OD. An opening 170 according to the diameter in the other end 171 is formed in the holder 17. The opening 170 is formed on the optical axis OA and light from the light source 13 is transmitted. Also, a member of such as, for example, aluminum, stainless steel, or engineering plastic, can be used as the holder 17.

The holder 17 integrated with the object lens 16 is moved in the optical axis direction OD with the object lens 16 by an object lens drive unit 19 (a drive unit). The object lens drive unit 19 is attached to the object lens 16 and moves the holder 17 in the optical axis direction of the object lens 16 so that the MO crystal 18 contacts the semiconductor device D. The object lens 16 is moved in the optical axis direction OD, so that it is possible to adjust a focus position of the object lens 16. Also, the holder 17 is moved in the optical axis direction OD, so that a distance between the holder 17 and the semiconductor device D is shortened and the MO crystal 18 held by the holder 17 can be pressed to (contact) the semiconductor device D. Also, the object lens drive unit 19 may have a mechanism which individually moves each of the holder 17 and the object lens 16. That is, a mechanism for individually moving the object lens 16 and the holder 17 (e.g., a slide mechanism) may be provided independently of a mechanism for integrally moving the object lens 16 and the holder 17. It is necessary to move the object lens 16 for focusing or the like in the optical axis direction OD after the MO crystal 18 and the semiconductor device D are in contact with each other. However, if the object lens 16 and the holder 17 are integrally moved in the optical axis direction OD after the contact, an excessive force may be applied to the MO crystal 18 and the semiconductor device D. In this regard, it is possible to relatively move the object lens 16 with respect to the MO crystal 18 by separating the movement of the object lens 16 and the movement of the holder 17 after the MO crystal 18 and the semiconductor device D are in contact with each other.

A ring-shaped flexible member 26 is provided in the other end 171 of the holder 17. An outer diameter of the flexible member 26 approximately matches that of the other end 171 of the holder 17 and the flexible member 26 is provided along a shape of the other end 171 of the holder 17. The flexible member 26 is interposed between the MO crystal 18 and the holder 17 in the optical axis direction OD and is fixed to both the MO crystal 18 and the holder 17. An inner diameter of the flexible member 26 is smaller than that in the other end 171 of the holder 17. Thereby, an opening 29 through which light is transmitted and which has a smaller region than the opening 170 is formed between the opening 170 and the MO crystal 18 in the flexible member 26. Because the region of the opening 29 is smaller than that of the opening 170, the flexible member 26 overlaps a part of the region of the opening 170 when viewed from the optical axis direction OD. The flexible member 26 is, for example, an elastic member configured to include rubber, a spring, or the like. Also, it is only necessary for the flexible member 26 to be any member having a shape which is deformed and the flexible member 26 may not necessarily be an elastic member.

The MO crystal 18 is fixed to the flexible member 26. The MO crystal 18 is located within a region of the opening 170 as viewed from the optical axis direction OD. That is, the MO crystal 18 is smaller than the region of the opening 170 and is located in a region overlapping the opening 170 in the optical axis direction OD. Consequently, the MO crystal 18 is fixed to a portion projecting from the holder 17 to the opening 170 (a portion overlapping the opening 170 as viewed from the optical axis direction OD) in the flexible member 26. The MO crystal 18 is disposed to face an irradiation plane of light in the semiconductor device D and its center is located on the optical axis OA.

Here, when the MO crystal 18 contacts the semiconductor device D, for example, the semiconductor device D may be inclined with respect to a plane orthogonal to the optical axis OA. In this case, if an incident plane of the MO crystal 18 is not inclined with respect to a plane orthogonal to the optical axis OA (or is inclined to an ignorable degree of inclination), a part of the MO crystal contacts the semiconductor device D in advance of the other part. If the object lens drive unit 19 is further moved in the same direction in this state, the flexible member 26 (particularly, the flexible member 26 in proximity to the part contacting the semiconductor device D in advance of the other part) is bent (bent, distorted, or stretched and, therefore, is deformed) and the other part of the MO crystal 18 is also pressed to the semiconductor device D so that it is shaped to the inclination of the semiconductor device D. That is, the flexible member 26 is bent (that is, the flexible member 26 is flexibly deformed), so that an incident plane 18i of the MO crystal 18 can be inclined with respect to the plane orthogonal to the optical axis OA. Also, even when the flexible member 26 causes the incident plane of the MO crystal 18 to be inclined by bending, a thickness, a degree of hardness, or the like is selected so that an inclination angle of the incident plane of the MO crystal 18 with respect to the plane orthogonal to the optical axis OA is less than or equal to an aperture angle of the object lens 16.

Also, an aperture angle θ of the object lens 16 is defined as a maximum angle with respect to the optical axis of the object lens 16 and the aperture angle θ is represented in the following Equation (1).

[Math. 1]

$$\theta = \pm \sin^{-1}\left(\frac{NA}{n}\right) \quad (1)$$

NA denotes a numerical aperture of the object lens 16 and n denotes a refractive index of a medium around the object lens 16. For example, when the numerical aperture NA of the object lens 16 is 0.14 and there is air in the vicinity of the object lens 16 (i.e., refractive index n=1), the aperture angle of the object lens 16 is about θ=±8.05°.

The MO crystal 18 changes a polarized state of light input from the incident plane 18i according to a magnetic field generated in the semiconductor device D by a magneto-optical effect. Thereby, for example, during a malfunction such as generation of a leakage current in the semiconductor device D, a change in a magnetic field different from that of the normal time due to the malfunction can be output as a polarized state of light. The polarized state of light is acquired as an intensity of light by the light sensor 20 to be described below. Details of the MO crystal 18 will also be described with reference to FIG. 3.

Figure 3:
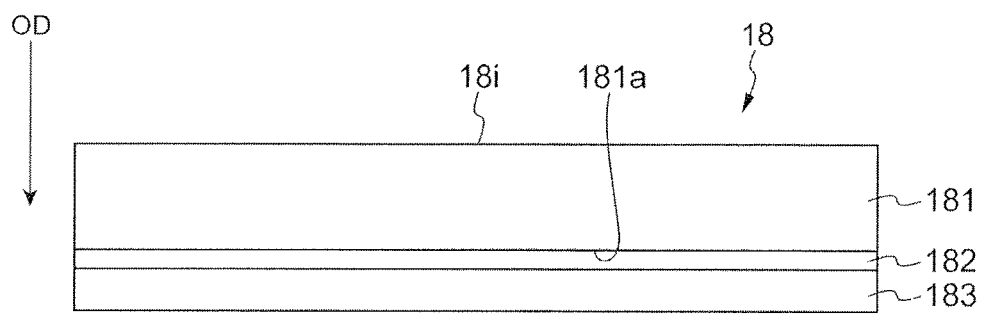
FIG. 3 is a diagram illustrating an MO crystal in the inspection device of FIG. 1.

As illustrated in FIG. 3, in the MO crystal 18, a thin film (e.g., about 1 μm) of a material (e.g., a magnetic garnet) for generating a magneto-optical effect is formed in another plane 181a opposite to the incident plane 18i in a crystal growth substrate 181 constituting the incident plane 18i of light and a magneto-optical effect layer 182 is formed. Because magnetism occurring in the semiconductor device D is efficiently incorporated in a plane opposite to the crystal growth substrate 181 in the magneto-optical effect layer 182, a metallic film of gold or the like is formed. The metallic film is a reflecting film 183 which also has a function of reflecting light incident from the incident plane 18i. Also, anti-reflection processing may be performed on the incident plane 18i of light in the crystal growth substrate 181. Thereby, it is possible to reduce interference noise due to interference of reflected light in the incident plane 18i and reflected light in the reflecting film 183. Also, the reflecting film 183 may be a material which transmits and reflects light of a wavelength of, for example, 1064 nm or more. In this case, for example, if light of 1300 nm is radiated to the MO crystal 18, a part of the light is transmitted through the reflecting film 183, reflected by the semiconductor device D, and detected. Also, for example, the reflecting film 183 may be a material which reflects a wavelength for observing a change in the magnetic field and transmits a wavelength for observing the semiconductor device D. In this case, for example, light of a wavelength transmitted through the MO crystal 18 is reflected by the semiconductor device D and detected and light of a wavelength reflected by the MO crystal 18 is reflected by the MO crystal 18 and detected. Thereby, even in a state in which the MO crystal 18 is located on the semiconductor device D, it is possible to place the MO crystal 18 in the semiconductor device D (cause the MO crystal 18 to contact the semiconductor device D) while viewing a measurement position in the semiconductor device D by imaging light transmitted through the MO crystal and reflected by the semiconductor device D.

Returning to FIG. 1, light output from the light source 13 is radiated to the MO crystal 18, reflected light reflected in the MO crystal 18 is returned to the light division optical system 14 via the object lens 16 and the optical scanner 15 and guided to the light sensor 20 optically coupled to the light division optical system 14 via an optical fiber for return light. The light sensor 20 is, for example, a photodiode, an avalanche photodiode, a photomultiplier tube, an area image sensor, or the like, receives reflected light from the MO crystal 18, and outputs a detection signal. The light sensor 20 has two detectors and detects an intensity of reflected light by detecting a difference between intensities of light input to the two detectors.

Figure 4:
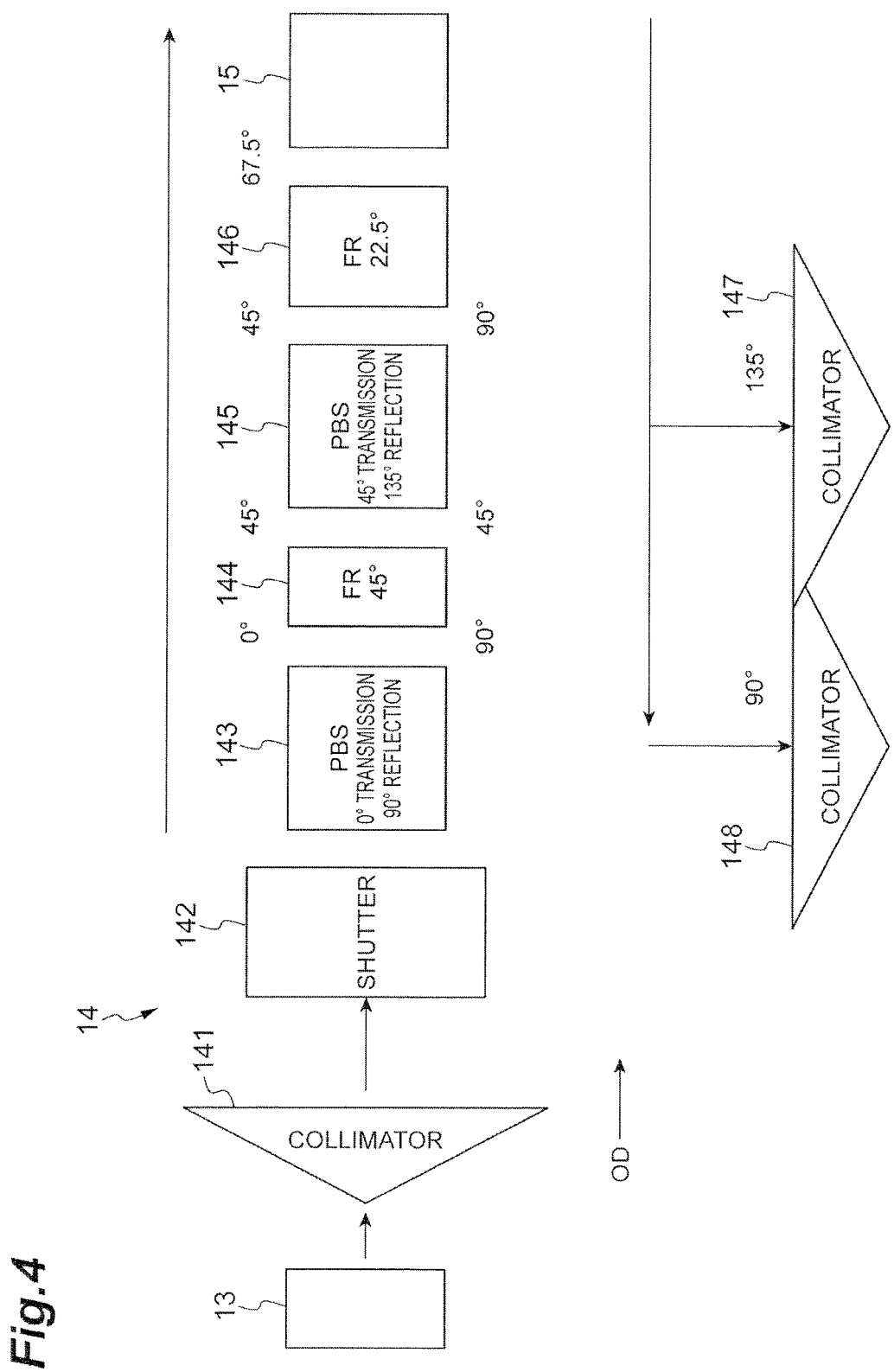
FIG. 4 is a diagram illustrating a light division optical system in the inspection device of FIG. 1.

Here, the light division optical system 14 will also be described with reference to FIG. 4. The light division optical system 14 is configured to include collimators 141, 147, and 148, a shutter 142, polarization beam splitters (hereinafter referred to as PBSs) 143 and 145, and Faraday rotators (hereinafter referred to as FRs) 144 and 146 and they are optically coupled. As illustrated in FIG. 4, when light from the light source 13 is radiated to the MO crystal 18 via the optical scanner 15, the light from the light source 13 is first input to the shutter 142 via the collimator 141. It is only necessary for the shutter 142 to control ON/OFF of light. Therefore, light output from the shutter 142 is input to the PBS 143. The PBS 143 is set to transmit light having a polarization component of 0 degrees and reflect light having a polarization component of 90 degrees. Also, the PBS 143 is set according to polarization of light from the shutter 142. Thus, the PBS 143 transmits light from the shutter 142. The light having the polarization component of 0 degrees transmitted through the PBS 143 is input to the FR 144 for inclining (rotating) a polarization plane of input light by 45 degrees and its polarization component becomes 45 degrees.

Light transmitted through the FR 144 is input to the PBS 145. The PBS 145 is set to transmit light of a polarization component of 45 degrees and reflect light of a polarization component of 135 degrees. Consequently, light transmitted through the FR 144 is transmitted through the PBS 145. Light transmitted through the PBS 145 is input to the FR 146 which inclines a polarization plane of input light by 22.5 degrees and input to the optical scanner 15 as light having a polarization component of 67.5 degrees. The light is radiated to the MO crystal 18.

For reflected light from the MO crystal 18, a polarization plane is rotated according to a Kerr effect or (and/or) a Faraday effect proportional to a magnetic Geld (a magnetic field intensity) occurring in the semiconductor device D. The reflected light has a polarization plane inclined by 22.5 degrees by the FR 146 and is input to the PBS 145. The reflected light is divided into light having a polarization component of 135 degrees and light having a polarization component of 45 degrees by the PBS 145. The light having the polarization component of 135 degrees is reflected by the PBS 145 and input to one light detector of the light sensor 20 via the collimator 147. It is possible to detect a signal of "half of an amount of return light (reflected light)+an amount of light according to the Kerr effect or the Faraday effect" from the light. On the other hand, the light having the polarization component of 45 degrees is transmitted through the PBS 145 and the polarization plane is inclined by 45 degrees by the FR 144, changed to light having a polarization component of 90 degrees, and input to the PBS 143. Light having the polarization component of 90 degrees is reflected by the PBS 143 and input to the other light detector of the light sensor 20 via the collimator 148. It is possible to detect a signal of "half of an amount of return light (reflected light)—an amount of light according to the Kerr effect or the Faraday effect" from the light. Therefore, it is possible to detect an optical signal according to the Kerr effect or the Faraday effect (a rotation amount of polarization) by detecting a difference between the two detectors of the light sensor 20. Thereby, it is possible to estimate a change in a magnetic field (a magnetic field intensity) occurring in the semiconductor device D and, for example, detect a change in the magnetic field different from that of the normal time due to a malfunction.

Returning to FIG. 1, the detection signal output from the light sensor 20 is amplified by the amplifier 21 and input as an amplification signal to the frequency analysis unit 12. The light sensor 20, the amplifier 21, and the frequency analysis unit 12 are electrically coupled. The frequency analysis unit 12 extracts a measurement frequency component in the amplification signal and outputs the extracted signal as an analysis signal. The measured frequency is set on the basis of, for example, a modulated frequency of a modulated current signal applied to the semiconductor device D. A lock-in amplifier, a spectrum analyzer, a digitizer, a cross domain analyzer (registered trademark), and the like can be used as the frequency analysis unit 12.

An analysis signal output by the frequency analysis unit 12 is input to the computer 22. The computer 22 is, for example, a PC or the like. An input device 24 such as a keyboard or a mouse by which a measurement condition or the like is input from the user and a display device 23 such as a monitor for showing a measurement result to a user are connected to the computer 22. The computer 22 includes a processor. The computer 22 executes a function of controlling the light source 13, the optical scanner 15, the object lens drive unit 19, the tester unit 11, the light sensor 20, the frequency analysis unit 12, and the like and a function of creating a magnetic distribution image, a magnetic frequency plot, or the like on the basis of the analysis signal from the frequency analysis unit 12 by a processor.

Next, a measurement procedure of the inspection device 1 will be described. The measurement procedure includes a procedure (a method) of disposing the MO crystal 18 held by the holder 17 via the flexible member 26 so that the MO crystal 18 faces the semiconductor device D.

First, the deposition of the MO crystal 18 in the semiconductor device D is confirmed using the object lens 16 to which the MO crystal 18 is not attached. The MO crystal 18 is disposed to avoid a position of an obstacle (particularly, wire bonding) on the semiconductor device D.

Subsequently, a turret (not illustrated) is controlled and the object lens 16 to which the MO crystal 18 is attached is set on the semiconductor device D, so that the MO crystal 18 is disposed on the optical axis of the object lens 16. Therefore, light of a wavelength at which the reflecting film 183 of the MO crystal 18 can transmit light is radiated from the light source 13 and the reflected light from the semiconductor device D is detected by the light sensor 20. On the basis of the detected light, a reflection image of an irradiation plane of the semiconductor device D is created. The object lens drive unit 19 is moved in the optical axis direction OD so that the distance between the MO crystal 18 and the semiconductor device D is gradually shortened while the reflection image is confirmed. Thereby, the MO crystal 18 contacts the semiconductor device D. If the object lens drive unit 19 has a slide mechanism or the like and the object lens 16 and the holder 17 can be individually moved, the holder 17 (i.e., the MO crystal 18) is prevented from being moved even when the object lens 16 is moved after the MO crystal 18 contacts the semiconductor device D. Thus, an excessive force is not applied from the MO crystal 18 to the semiconductor device D and it is possible to press the MO crystal 18 to the semiconductor device D according to an own weight of the MO crystal 18 or a force of an elastic member such as a spring separately provided between the object lens 16 and the holder 17.

In a state in which the MO crystal 18 contacts the semiconductor device D, the flexible member 26 is bent (deformed) so that approximately the entire bottom of the MO crystal 18 follows the irradiation plane (a device plane) of the semiconductor device D and the bottom and the incident plane 18i of the MO crystal are inclined with respect to a plane orthogonal to the optical axis OA of the object lens 16. If the flexible member 26 is an elastic member, the MO crystal 18 easily follows the semiconductor device D according to a repulsive force of the elastic member. Thereby, a gap between the MO crystal 18 and the semiconductor device D can be minimized and the improvement of resolution and the improvement of S/N are implemented.

After the MO crystal 18 is set on the semiconductor device D, a current signal is applied from the tester unit 11 to the semiconductor device D. If the lock-in detection is performed, a modulated current signal is applied to the semiconductor device D. Therefore, light is radiated from the light source 13 to the MO crystal 18 via the optical scanner 15. A wavelength of the light may be the same as a wavelength of light when the MO crystal 18 is set on the above-described semiconductor device D and the light may be light of a wavelength further reflected in the reflecting film 183 of the MO crystal 18. Also, the light may be CW light or pulse light. Also, if light of a wavelength capable of being transmitted through the reflecting film 183 of the MO crystal 18 is used, light reflected by the irradiation plane (the device plane) of the semiconductor device D and light reflected by the MO crystal 18 interfere with each other and may serve as noise. Thus, it is preferable to reduce noise due to interference by radiating incoherent light.

Subsequently, light reflected from the MO crystal 18 is detected by the light sensor 20 and a detection signal is output. At this time, the light division optical system 14 including the two PBSs 143 and 145 and the two FRs 144 and 146 and the two light detectors of the light sensor 20 perform differential detection. Subsequently, the detection signal is amplified by the amplifier 21 and serves as the amplification signal. Subsequently, the frequency analysis unit 12 outputs a signal of a measurement frequency component of the amplification signal as an analysis signal. The measurement frequency component is set on the basis of a frequency of the modulated current signal. Also, if no lock-in detection is performed, it is unnecessary to output a signal of a specific frequency component and the amplification signal is output as an analysis signal as it is.

Therefore, the computer 22 controls the optical scanner 15 such that it changes an optical irradiation position in the MO crystal 18 and scans the irradiation of light in a direction of the incident plane 18i of the MO crystal 18. As described above, it is possible to obtain a two-dimensional magnetic field distribution by iterating the detection of reflected light from the MO crystal 18 while changing a light irradiation position. Also, if a frequency property of a magnetic field at a certain position is viewed, it is only necessary to view a measurement frequency, switch it within a frequency band, and acquire a magnetic frequency plot. Also, it is only necessary to change an optical spot diameter or a scanning range and iterate the above-described process to obtain a magnetic field intensity distribution of higher resolution.

Next, an operation and an effect of the inspection device 1 according to the present embodiment will be described.

Conventionally, technology for detecting a generation position (a leakage path) of a leakage current using an optical beam induced resistance change (OBIRCH) method of radiating laser light to the measurement object and detecting a resistance value change due to temperature generated by the laser light is known. Here, the OBIRCH method is characterized in that the resistance value change is detected, but the resistance change due to the temperature is small if current bypass resistance (leakage resistance) is significantly small and detection is difficult. Also, even when wiring through which the leakage current flows is below other wiring, detection is difficult in the OBIRCH method. There is also a method of detecting the leakage path from a heat generation image, but the detection may be difficult for a reason similar to that of the OBIRCH method. Consequently, a method of acquiring the leakage path in a method other than the OBIRCH method is desired.

Figure 13:
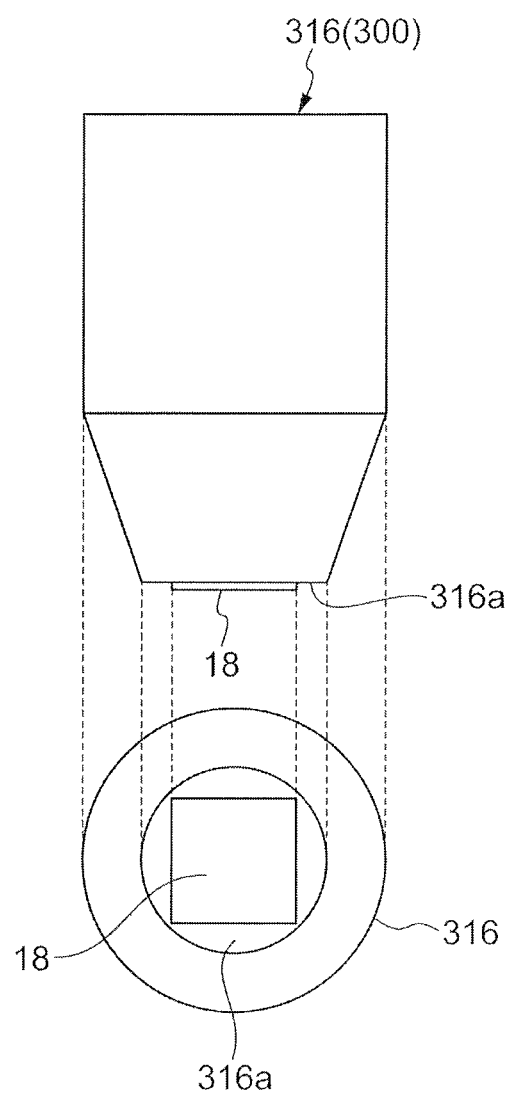
FIG. 13 is a diagram illustrating an inspection device according to a comparative example.

As another method, there is a method of acquiring a detection signal by detecting reflected light using a magnetic-optical effect of the MO crystal. In this method, for example, as illustrated in FIG. 13, the MO crystal 18 is fixed to a lens plane 316a of the object lens 316 for use in light concentration and the object lens 316 is in proximity to the measurement object, so that a magnetic field occurring in the measurement object is measured. However, if the measurement object is inclined, a distance between the measurement object and the MO crystal 18 may not be sufficiently short. In this case, the detection accuracy of the detection signal may be degraded due to the deterioration of detection sensitivity or the like.

Figure 5:
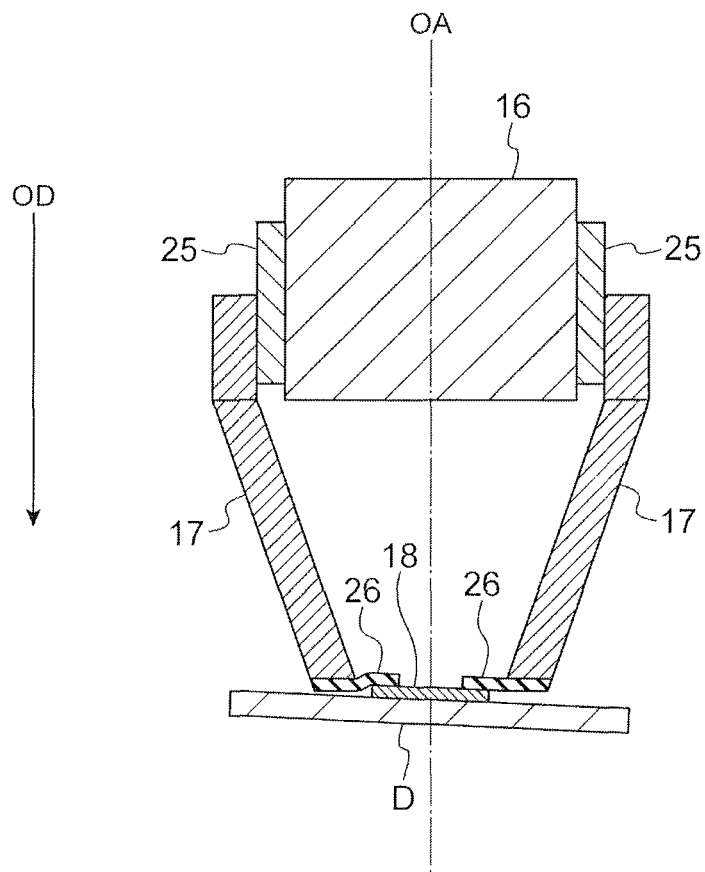
FIG. 5 is a diagram illustrating an operation and an effect of the inspection device of FIG. 1.

In this regard, when the MO crystal 18 contacts the semiconductor device D in the inspection device 1 according to the present embodiment, the flexible member 26 is bent and therefore the incident plane 18i of light of the MO crystal 18 can be inclined with respect to the plane orthogonal to the optical axis OA. Here, for example, if the semiconductor device D is inclined with respect to the plane orthogonal to the optical axis OA, a part of the MO crystal 18 to be moved by the object lens drive unit 19 which moves in the optical axis direction OD is pressed to the semiconductor device D in advance of the other part. In this state, if the MO crystal 18 is further pressed to the semiconductor device D, the flexible member 26 (particularly, the flexible member 26 in proximity to the MO crystal 18 pressed to the semiconductor device D in advance thereof) is bent (deformed) and other part of the MO crystal 18 is also pressed to the semiconductor device D while being shaped to the inclined semiconductor device D (see FIG. 5). That is, it is possible to set the incident plane 18i of light of the MO crystal 18 at an angle according to the inclination of the semiconductor device D (along the inclination) using flexibility of the flexible member 26. Thereby, a state in which the semiconductor device D and the MO crystal 18 are in contact with each other (or a state in which they are in proximity to each other) can be brought about and a magnetic field property occurring in the semiconductor device D can be appropriately measured using the MO crystal 18. Also, because an inclination angle of the incident plane 18i of the MO crystal 18 with respect to the plane orthogonal to the optical axis OA is less than or equal to an aperture angle of the object lens 16, it is possible to reliably detect light reflected by the MO crystal 18 in the object lens 16. From the above, in the case in which the semiconductor device D is inclined or the like, it is possible to improve the detection accuracy of the detection signal by setting a state in which the semiconductor device D and the MO crystal 18 are in contact with each other (or a state in which they are in proximity to each other).

Also, the flexible member 26 is interposed between the holder 17 and the MO crystal 18 in the optical axis direction OD (i.e., a direction in which the holder 17 and the MO crystal 18 held by the holder 17 move), so that the flexible member 26 can be appropriately bent according to a force generated by contacting when the MO crystal 18 moved in the optical axis direction OD contacts the semiconductor device D. Thereby, the semiconductor device D and the MO crystal 18 can be more easily brought into contact with each other.

Also, an opening 170 through which light from the light source 13 is transmitted is formed in the holder 17 and the MO crystal 18 is interposed within a region of the opening 170 when viewed from the optical axis direction OD. Thereby, when the MO crystal 18 which moves in the optical axis direction OD contacts the semiconductor device D, the flexible member 26 is bent, so that it is possible to move the MO crystal 18 to the inside of the opening 170. Thus, it is possible to more appropriately press the MO crystal 18 shaped to the inclination of the semiconductor device D by releasing the MO crystal 18 to the opening 170.

Also, an opening 29 through which the light is transmitted between the opening 170 and the MO crystal 18 is formed in the flexible member 26. The opening 29 is formed, so that the flexible member 26 can be bent more easily than when no opening is formed in the flexible member. Also, because it is possible to view the MO crystal 18 from the opening 29, it is possible to easily cause the MO crystal 18 to contact the semiconductor device D.

Also, the holder 17 is attached to the object lens 16 and the object lens drive unit 19 may move the holder 17 in the optical axis direction OD of the object lens 16 and cause the MO crystal 18 to contact the semiconductor device D by moving the object lens 16 in the optical axis direction OD. Thereby, the movement of the object lens 16 and the movement of the holder 17 can be simultaneously performed.

Also, light output from the light source 13 is incoherent light, so that it is possible to reduce noise due to interference of light within the MO crystal 18 and between the MO crystal 18 and the semiconductor device D.

Also, because the MO crystal 18 reflects a part of light and transmits a part of the light, it is possible to cause the MO crystal 18 to contact the semiconductor device D while viewing a measurement position in the semiconductor device D.

Also, the flexible member 26 is configured to include an elastic member of such as rubber or a spring. Thereby, it is possible to appropriately bend the flexible member 26 and easily set a state in which the semiconductor device D and the MO crystal 18 are in contact with each other (or a state in which they are in proximity to each other).

[Second Embodiment]

Next, an inspection device according to the second embodiment will be described with reference to FIG. 6. Also, differences from the above-described first embodiment will be mainly described in the description according to the second embodiment.

Figure 6:
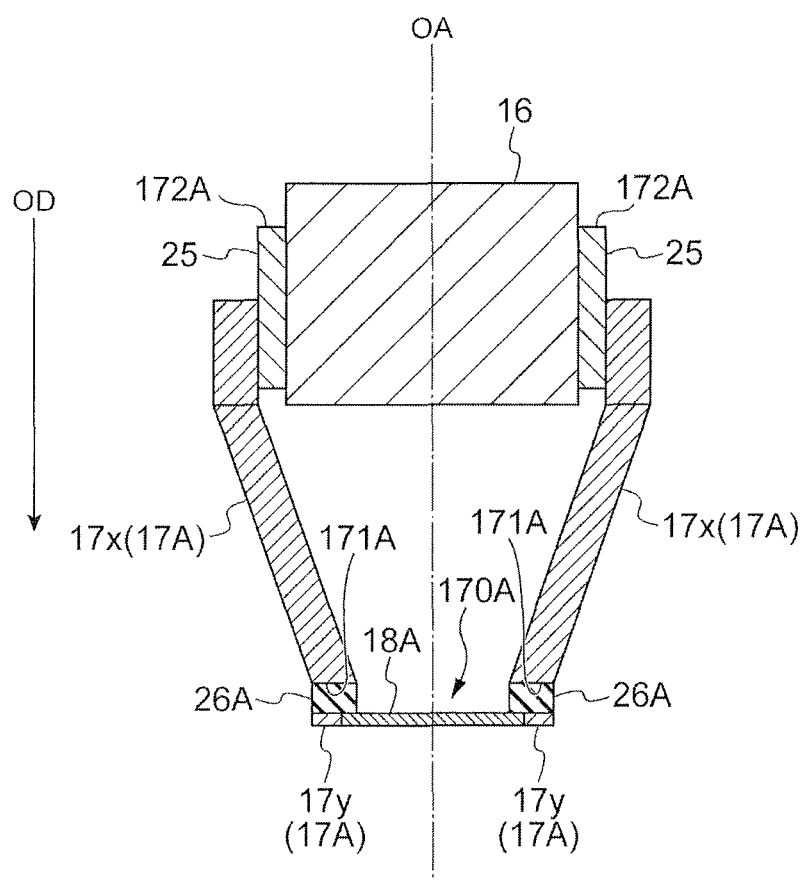
FIG. 6 is a cross-sectional view of a holder unit in an inspection device of a second embodiment of the present invention.

As illustrated in FIG. 6, the present embodiment is different from the above-described first embodiment in that a holder 17A includes two holding units of a holder 17y (a first holding unit) which directly holds an MO crystal 18A and a holder 17x (a second holding unit) which holds the holder 17y via a flexible member 26A. The holder 17x has a shape similar to that of the holder 17 according to the first embodiment. That is, the holder 17x is fixed to an adaptor 25 in a state in which an internal surface of one end 172A in the optical axis direction OD is in contact with an external surface of the adaptor 25 and has approximately a truncated cone shape in which a diameter decreases from one end 172A to the other end 171A. In the holder 17A, an opening 170A according to the diameter in the other end 171A is formed. Further, a ring-shaped flexible member 26A is provided along a shape of the other end 171A in the other end 171A of the holder 17x. An outer diameter and an inner diameter of the flexible member 26A approximately match an outer diameter and an inner diameter of the other end 171A of the holder 17A.

The holder 17y is fixed to the flexible member 26A. The holder 17y has a ring shape and its outer diameter approximately matches that of the flexible member 26A. Therefore, the MO crystal 18A is fixed to an inner circumferential surface of the holder 17y. Thereby, the MO crystal 18A is directly held (supported) by the holder 17y.

As described above, the holder 17A is constituted of two holding units of the holder 17y and the holder 17x, so that the contacting of the MO crystal 18A against the semiconductor device D can be performed according to a shape or an inspection region of the semiconductor device D. That is, unlike with the case in which the MO crystal is held by one holder, the inspection according to the semiconductor device D is enabled. Also, it is possible to flexibly determine the position of the flexible member 26A and the like. Further, because it is possible to make a configuration in which the flexible member 26A and the MO crystal 18A are not in direct contact with each other (a configuration in which the holder 17y fixed to the flexible member 26 holds the MO crystal 18A), it is possible to make a configuration in which the flexible member 26A and the MO crystal 18A do not overlap (or an overlapping region is small) when viewed from the optical axis direction OD. Thereby, when the MO crystal 18A contacts the semiconductor device D, it is possible to avoid the difficulty of viewing the MO crystal 18A due to the flexible member 26A.

[Third Embodiment]

Next, an inspection device according to the third embodiment will be described with reference to FIG. 7. Also, differences from the above-described first embodiment will be mainly described in the description of the third embodiment.

Figure 7:
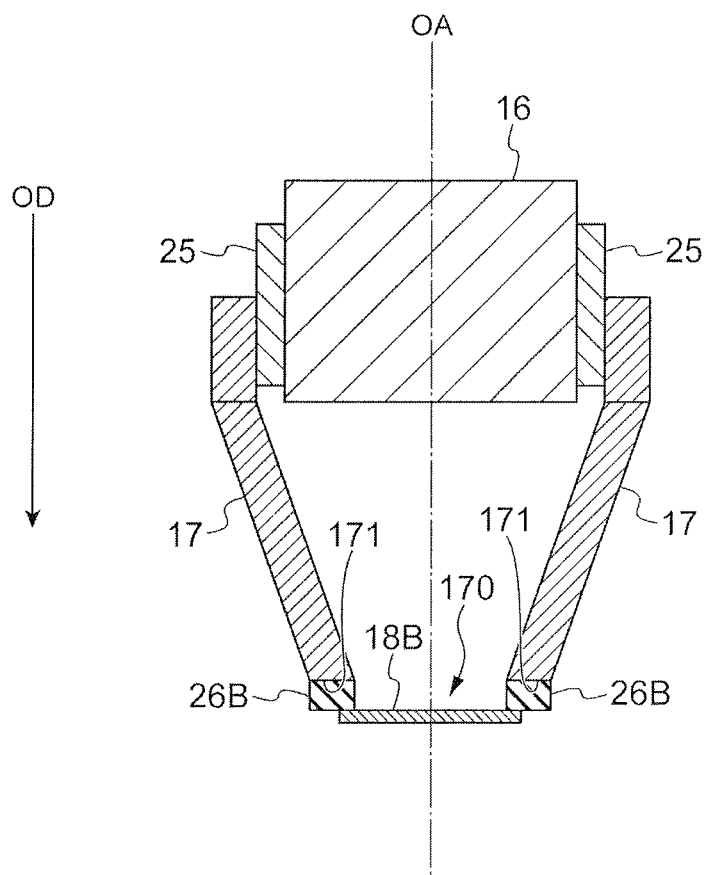
FIG. 7 is a cross-sectional view of a holder unit in an inspection device of a third embodiment of the present invention.

As illustrated in FIG. 7, the present embodiment is different from the above-described first embodiment in that an MO crystal 18B located in a region overlapping an opening 170 in an optical axis direction OD is larger than a region of the opening 170 of the holder 17 and a flexible member 26B fixed to the other end 171 of the holder 17 is formed of a thicker member than the above-described flexible member 26. Specifically, relatively thick high-resilience sponge or the like is used as the flexible member 26B.

The MO crystal 18B is larger than a region of the opening 170, so that it is possible to enlarge a range in which the semiconductor device D can be inspected without moving the MO crystal 18 as compared with the case in which the MO crystal 18 smaller than the region of the opening 170 is used. However, if the MO crystal 18 larger than the region of the opening 170 is used, the MO crystal 18B cannot be released to the opening 170 when the MO crystal 18B contacts the semiconductor device D and the MO crystal 18B may not be appropriately pressed to the semiconductor device D. In this regard, because the flexible member 26B serves as relatively thick high-resilience sponge in the present embodiment, it is possible to increase an amount of deformation of the flexible member 26B. Thus, even when the MO crystal 18B cannot be released to the opening 170, the flexible member 26B is significantly deformed and therefore it is possible to appropriately press the MO crystal 18B to the semiconductor device D.

[Fourth Embodiment]

Next, an inspection device according to the fourth embodiment will be described with reference to FIG. 8. Also, differences from the above-described first embodiment will be mainly described in the description of the fourth embodiment.

Figure 8:
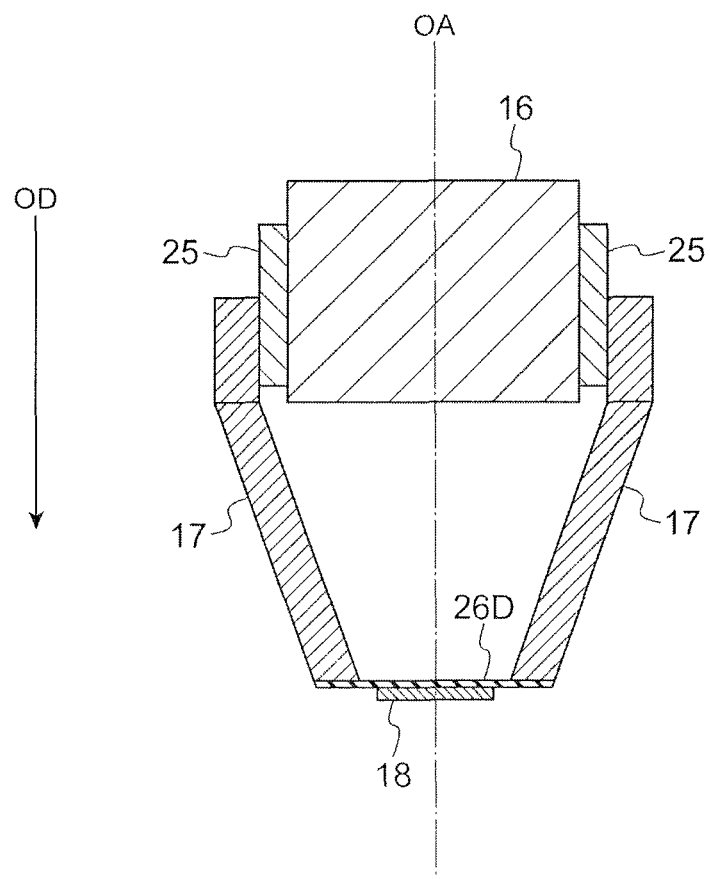
FIG. 8 is a cross-sectional view of a holder unit in an inspection device of a fourth embodiment of the present invention.

As illustrated in FIG. 8, the present embodiment is different from the above-described first embodiment in that no opening is formed in a flexible member 26D and the flexible member 26D is a relatively thin elastic film having optical transparency.

As described above, no opening is formed in the flexible member 26D, so that an operation of attaching the flexible member 26 to the holder 17 is facilitated. Here, if no opening through which light is transmitted is provided in the flexible member 26D, when there is a problem in that it is difficult to view the MO crystal 18, the flexible member 26D becomes a thin elastic film having optical transparency and therefore it is possible to view the MO crystal 18 without a problem. That is, it is possible to easily cause the MO crystal 18 to contact the semiconductor device D.

Although embodiments of the present invention has been described above, the present invention is not limited to the above-described embodiments.

Figure 9:
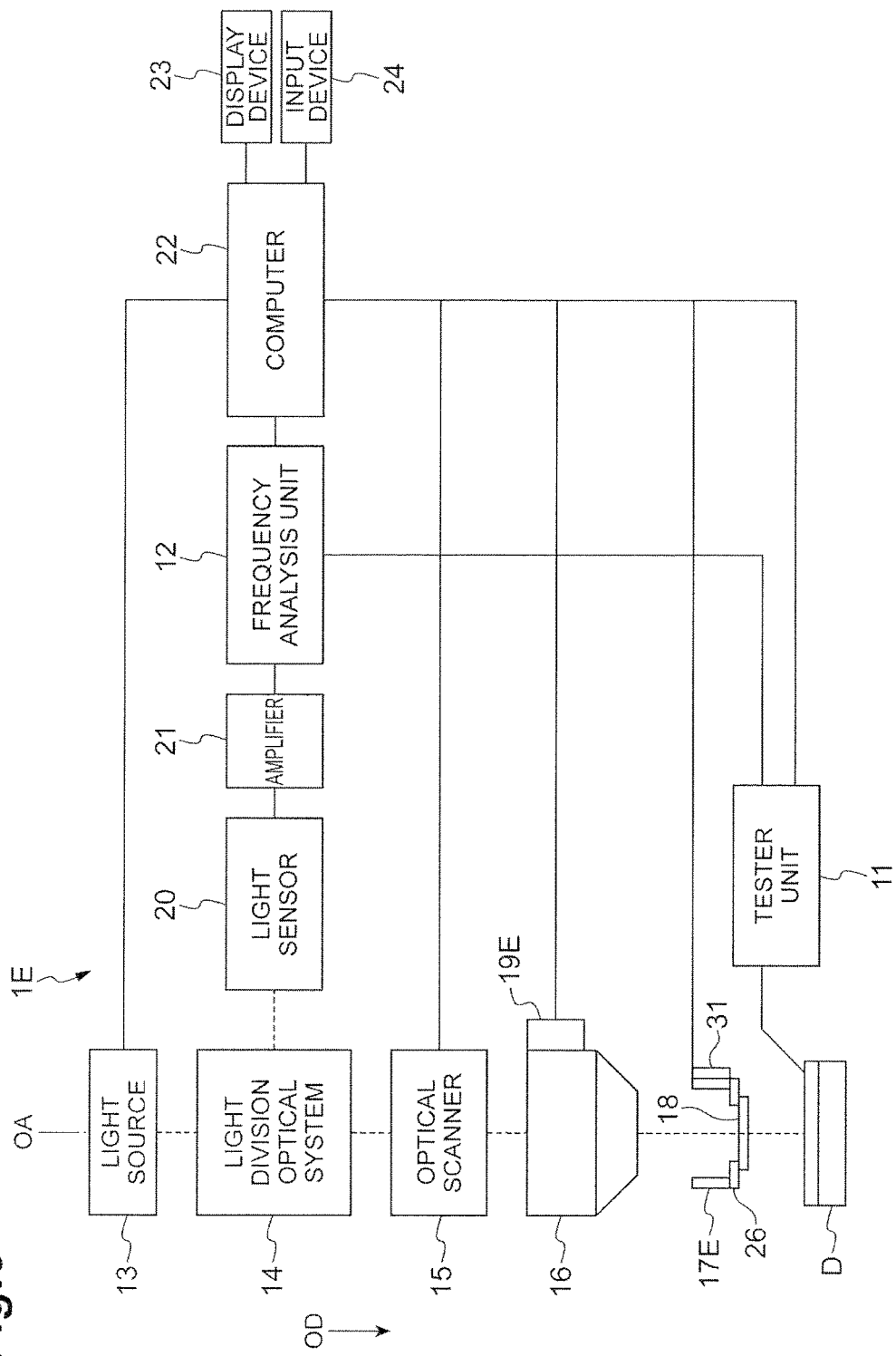
FIG. 9 is a configuration diagram of an inspection device according to a modified example.

Although an example in which the object lens drive unit 19 integrally moves the object lens 16 and the holder 17 has been described, the present invention is not limited thereto. As illustrated in FIG. 9, a holder drive unit 31 (a drive unit) which individually moves a holder 17E may be provided independently of an object lens drive unit 19E which moves the object lens 16. The holder drive unit 31 is attached to the holder 17 and the holder 17 is moved in the optical axis direction of the object lens 16 so that the MO crystal 18 contacts the semiconductor device D. In this case, the holder 17E can be moved in the optical axis direction OD and a plane direction orthogonal to the optical axis direction OD by the holder drive unit 31, the holder 17E can be inserted between the object lens 16 and the semiconductor device D, and the MO crystal 18 can be disposed on the optical axis of the object lens 16. Therefore, the holder drive unit 31 is controlled by the computer 22 and moved in the optical axis direction OD and therefore the MO crystal 18 can be pressed to the semiconductor device D.

Figure 10:
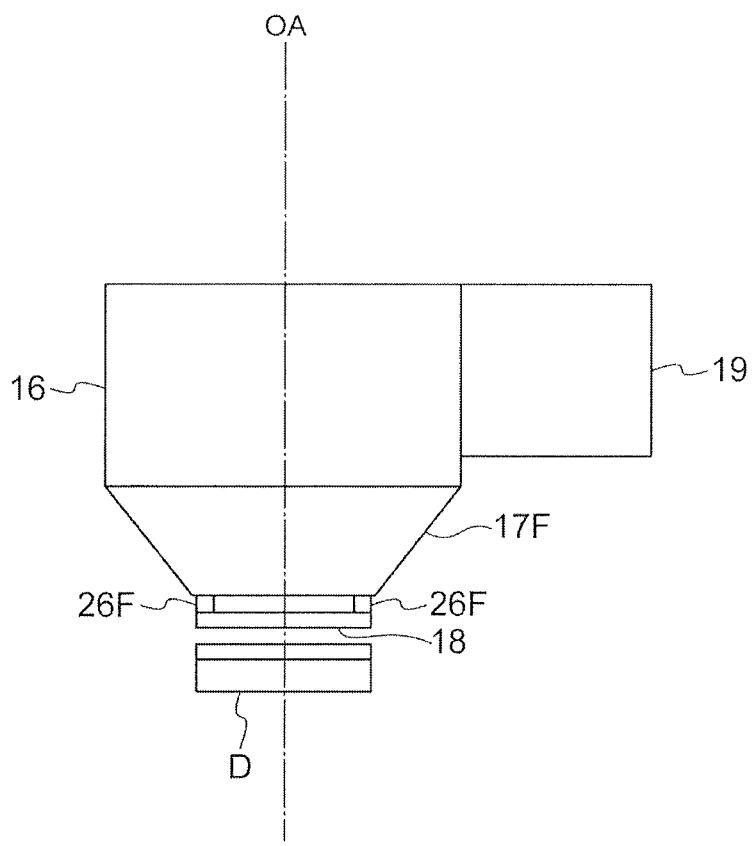
FIG. 10 is a diagram schematically illustrating a holder unit of the inspection device according to a modified example.

Also, the configuration of the holder unit is not limited to the above-described embodiment. As illustrated in FIG. 10, a configuration in which a barrel of the object lens 16 has a function of a holder 17F and an elastic member 26F is fixed to the holder 17F may be made. In this case, the MO crystal 18 is fixed to a lower surface of the elastic member 26F.

Figure 11:
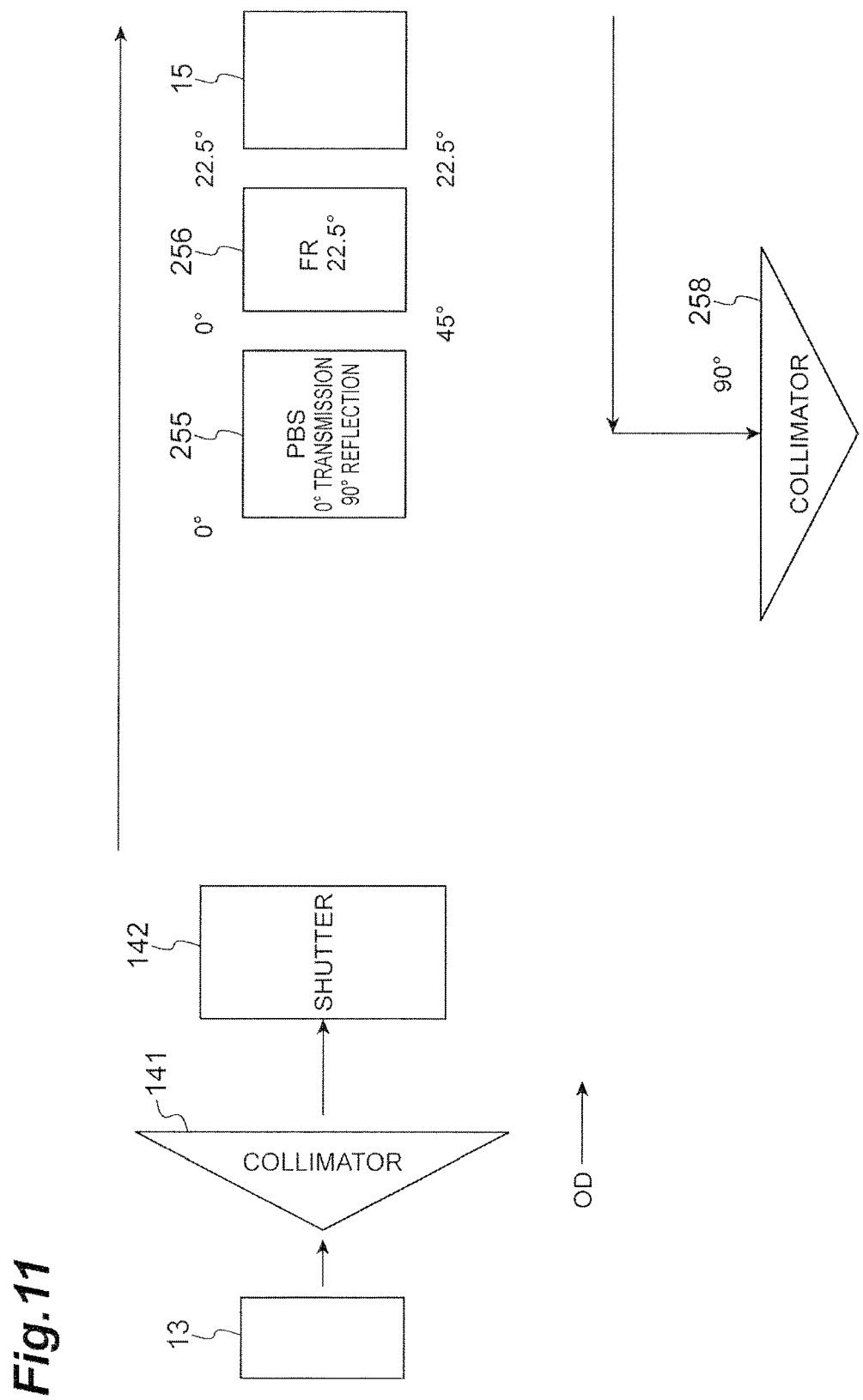
FIG. 11 is a diagram illustrating a light division optical system of the inspection device according to a modified example.

Also, as in a light division optical system 14x illustrated in FIG. 11, it is possible to omit one PBS and one FR from the configuration of FIG. 4. The light division optical system 14x is configured to include collimators 141 and 258, a shutter 142, a PBS 255, and an FR 256. In this case, first, light from the light source 13 is input to the shutter 142 via the collimator 141. Light output from the shutter 142 is input to the PBS 255. The PBS 255 is set to transmit light having a polarization component of 0 degrees and reflect light having a polarization component of 90 degrees. The light having the polarization component of 0 degrees transmitted through the PBS 255 is input to the FR 256 which inclines (rotates) a polarization plane of input light by 22.5 degrees and is radiated to the MO crystal 18 and the semiconductor device D. For reflected light from the MO crystal 18, a polarization plane is rotated according to a Kerr effect or a Faraday effect proportional to a magnetic field (a magnetic field intensity) occurring in the semiconductor device D. The reflected light has a polarization plane inclined by 22.5 degrees by the FR 256 and is reflected by the PBS 255. The reflected light is input to the light sensor via the collimator 258. Thereby, a detection signal to be detected as described above is not subjected to differential detection as in the example illustrated in FIG. 4, but there is no problem due to sufficiently increasing an S/N ratio of light from the light source 13.

Also, in the configuration of the light division optical system 14 illustrated in FIG. 4, a λ/4 plate may be provided at a position to which the optical scanner 15 is closer than the PBS 145. In this case, because light transmitted through the λ/4 plate becomes circular polarization and return light is inclined by 90 degrees, but reciprocatingly inclined by 45 degrees by the FR 146, it is possible to appropriately detect an optical signal as in the example illustrated in FIG. 4. Likewise, in a configuration of a light division optical system 14x illustrated in FIG. 11, a λ/4 plate may be provided at a position to which the optical scanner 15 is closer than the PBS 255. Even in this case, the return light is inclined by 90 degrees and a polarization component to be detected is also inclined by 90 degrees, but there is no problem in detecting the rotation of a polarization plane.

Figure 12:
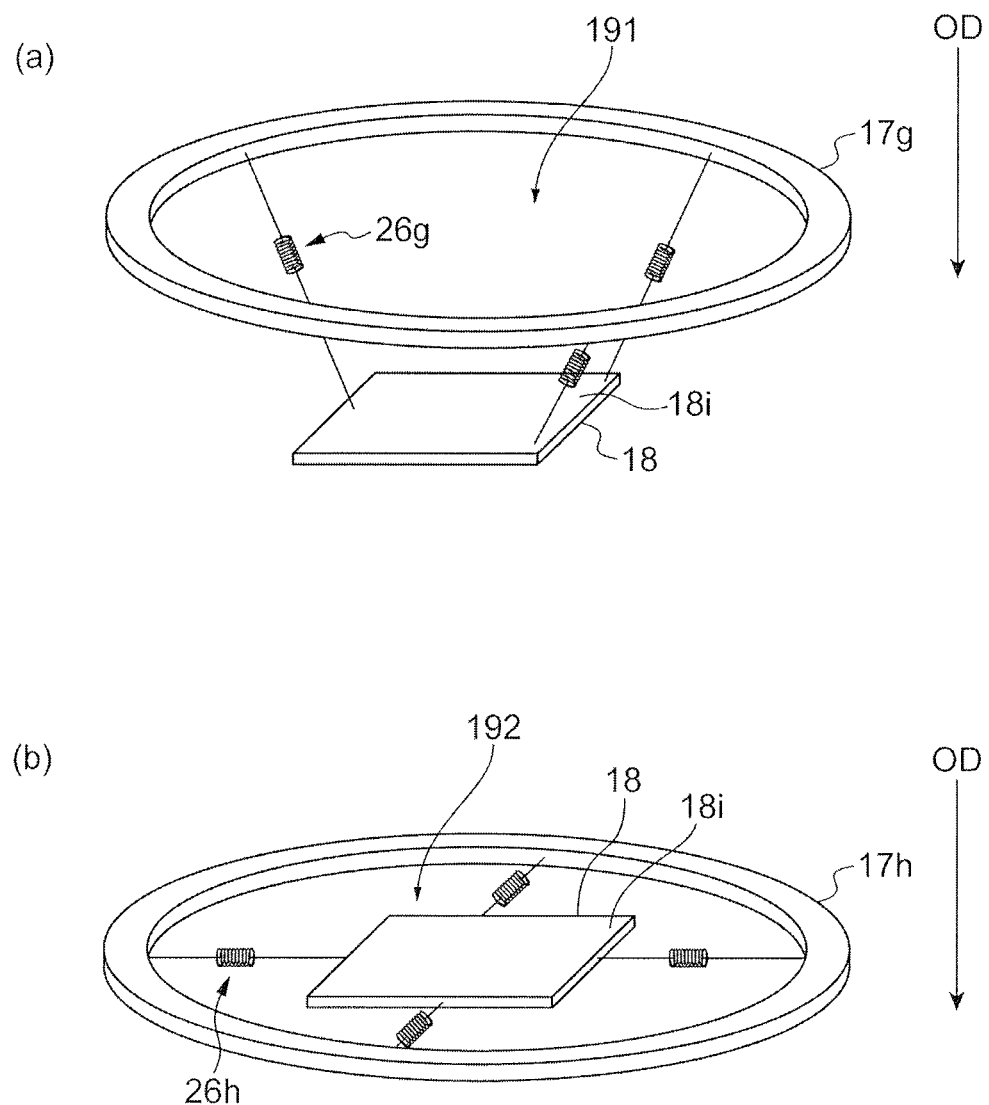
FIG. 12 is a diagram illustrating a flexible member of the inspection device according to a modified example.

Also, as illustrated in FIG. 12(*a*), a rectangular MO crystal 18 may be configured to be held by the holder 17g of a hollow cylindrical shape (or a ring shape) and hairsprings 26g. Also, the MO crystal 18 smaller than a region of an opening 191 of the holder 17g is used. That is, one end of each of three hairsprings 26g is fixed to an inner circumferential surface of the holder 17g and the other end of each of the three hairsprings is fixed to the MO crystal 18. Specifically, one end of each of the three hairsprings 26g are fixed to the inner circumferential surface of the holder 17g at approximately equal intervals. Also, the other end of one of the three hairsprings 26g is fixed in the vicinity of the center of one side of the incident plane 18i of the MO crystal and the other ends of the remaining two hairsprings are fixed in the vicinity of both ends of a side opposite to the above-described one side in the incident plane 18i of the MO crystal 18. Thus, the incident plane 18i of the MO crystal 18 is fixed to the three hairsprings 26g extending from the inner circumferential surface of the holder 17g, so that the MO crystal 18 can be disposed within a region of the opening 191 when viewed from the optical axis direction OD. Thereby, when the MO crystal 18 contacts the semiconductor device D, it is possible to release the MO crystal 18 to the opening 191 and appropriately press the MO crystal 18 shaped to the inclination of the semiconductor device D. Also, because the three hairsprings 26g are fixed to the vicinity of the center of one side among opposite sides in the MO crystal 18 and both ends of the other side, the incident plane 18i of the MO crystal 18 and a plane orthogonal to the optical axis OA are easily made approximately parallel to each other (a state in which the MO crystal 18 is not inclined) in a state in which the holder 17g supports the MO crystal 18. Thereby, it is possible to appropriately press the MO crystal 18 to the semiconductor device D. Also, although three hairsprings 26g are illustrated in FIG. 12(*a*), the MO crystal 18 may be held by more than three hairsprings 26g.

Also, as illustrated in FIG. 12(*b*), a rectangular MO crystal 18 may be configured to be held by a holder 17h of a hollow cylindrical shape (or a ring shape) and hairsprings 26h. Also, the MO crystal 18 smaller than a region of the opening 192 of the holder 17h is used. That is, one end of each of four hairsprings 26h is fixed to an inner circumferential surface of the holder 17h and the other ends of the four hairsprings 26h are fixed to the sides of the rectangular MO crystal 18. In a state in which the four hairsprings 26h having the same length and of the same material, in which one end is fixed to the inner circumferential surface of the holder 17h, and the other end is fixed to a side of the MO crystal 18 are used, the length and the material are determined so that a plane in which the holder 17h is disposed and a plane in which the MO crystal 18 is disposed approximately match each other. Thus, each side of the MO crystal 18 is fixed to the four hairsprings 26h extending from the inner circumferential surface of the holder 17h, so that it is possible to dispose the MO crystal 18 within the region of the opening 192 when viewed from the optical axis direction OD. Thereby, when the MO crystal 18 contacts the semiconductor device D, it is possible to release the MO crystal 18 to the opening 192 and appropriately press the MO crystal 18 shaped to the inclination of the semiconductor device D. Also, because the MO crystal 18 is disposed to approximately be coincident with a plane in which the holder 17h is disposed, the incident plane 18i of the MO crystal 18 and a plane orthogonal to the optical axis OA are easily made approximately parallel to each other (a state in which the MO crystal 18 is not inclined) in a state in which the holder 17h supports the MO crystal 18. Thereby, it is possible to appropriately press the MO crystal 18 to the semiconductor device D. Also, although four hairsprings 26h are illustrated in FIG. 12(b), the MO crystal 18 may be held by more than three or four hairsprings 26h.

Also, although the case in which the holder 17 has approximately a truncated cone shape having the optical axis OA as the center of the diameter thereof has been described, the shape of the holder unit is not limited thereto and may be, for example, a cylindrical shape in which a diameter does not change. Also, the holder unit may be a pair of arm members extending in the optical axis direction from both ends of an attachment unit attached to the object lens in a width direction. In this case, a flexible member is provided in a distal end of each of the pair of arm members (an end portion opposite to a side attached to the attachment unit) and the MO crystal is fixed to each flexible member, so that the pressing of the MO crystal to the above-described semiconductor device and the deformation of the flexible member are implemented. Further, the holder unit has approximately a truncated cone shape or a cylindrical shape and a connection unit which divides the opening may be configured to be provided in a circular opening formed at an end portion of a side for holding the MO crystal. The connection unit is assumed to radially extend toward an inner circumferential surface of the holder from the center of the opening, for example, so that the opening is divided into three regions having approximately a fan shape. At a point which intersects each connection unit (i.e., a center of the opening), the MO crystal may be configured to be fixed to the flexible member by providing a pillar part extending in the optical axis direction from each connection unit and further providing the flexible member at a distal end of the pillar part. According to the configuration, the pressing of the MO crystal to the above-described semiconductor device and the deformation of the flexible member are implemented.

Also, although an example of the object lens 16 as the lens unit is shown, the present invention is not limited thereto. For example, a plurality of lenses may be held and may be switchable via turrets.

REFERENCE SIGNS LIST

1 Inspection device
13 Light source
15 Optical scanner
16 Object lens (lens unit)
17, 17A, 17E, 17F Holder (holder unit)
18, 18A, 18B MO crystal
18i Incident plane
19, 19E Object lens drive unit (drive unit)
26, 26A, 26B, 26D, 26F Flexible member
29 Opening
31 Holder drive unit (drive unit)
170, 170A Opening
OD Optical axis direction

The invention claimed is:

1. An inspection device comprising:
a light source configured to output light;
a magneto-optical crystal disposed to face a measurement object;
a lens configured to concentrate the light onto the magneto-optical crystal;
a holder configured to hold the magneto-optical crystal;
a flexible member interposed between the magneto-optical crystal and the holder; and
a drive configured to cause the magneto-optical crystal to contact the measurement object by moving the holder in an optical axis direction of the lens,
wherein the flexible member bends to enable an incident plane to incline in a range in which an inclination angle of the incident plane of the light in the magneto-optical crystal with respect to a plane orthogonal to the optical axis is equal to or less than an aperture angle of the lens when the magneto-optical crystal contacts with the measurement object, and
wherein the magneto-optical crystal has a reflective film on a surface in contact with the measurement object, reflecting a part of the light and transmitting a part of the light.

2. The inspection device according to claim 1, wherein the flexible member is interposed between the holder and the magneto-optical crystal in the optical axis direction.

3. The inspection device according to claim 2,
wherein an opening through which the light from the light source is transmitted is formed in the holder, and
wherein the magneto-optical crystal is interposed within a region of the opening as viewed from the optical axis direction.

4. The inspection device according to claim 3, wherein an opening through which the light is transmitted between the opening and the magneto-optical crystal is formed in the flexible member.

5. The inspection device according to claim 1,
wherein the holder is attached to the lens, and
wherein the driver moves the holder in the optical axis direction of the lens and causes the magneto-optical crystal to contact the measurement object by moving the lens in the optical axis direction.

6. The inspection device according to claim 1, wherein the light is incoherent light.

7. The inspection device according to claim 1, wherein a wavelength of the light is 1064 nm or more.

8. The inspection device according to claim 1, wherein the flexible member has elasticity.

9. The inspection device according to claim 1, further comprising:
an optical scanner, the optical scanner scanning light across a selected region on an incident plane of the magneto-optical crystal.

10. The inspection device according to claim 1, wherein a modulated current is applied to the object, and lock-in detection is performed to detect measured light at a specific frequency.

11. The inspection device according to claim 1, wherein the reflecting film is a material which reflects a wavelength for observing a change in the magnetic field and transmits a wavelength for observing the semiconductor device.

12. The inspection device according to claim 1, wherein the reflecting film is a material which transmits and reflects light of a wavelength of 1064 nm or more.

13. A method of disposing a magneto-optical crystal facing a measurement object, wherein a holder holds the magneto-optical crystal via a flexible member, the method comprising:
disposing the magneto-optical crystal on an optical axis of an object lens;

causing the magneto-optical crystal to contact the measurement object by moving the holder in an optical axis direction of the object lens; and inclining an incident plane in a range in which an inclination angle of the incident plane of the light in the magneto-optical crystal with respect to a plane orthogonal to the optical axis is equal to or less than an aperture angle of the object lens by bending the flexible member when the magneto-optical crystal contacts the measurement object, wherein the magneto-optical crystal has a reflective film on a surface in contact with the measurement object, reflecting a part of the light and transmitting a part of the light.

* * * * *